United States Patent
Sitomer et al.

(10) Patent No.: US 7,877,270 B2
(45) Date of Patent: Jan. 25, 2011

(54) SYSTEMS AND METHODS FOR PROFILING CLINIC WORKFLOW

(75) Inventors: Joseph Sitomer, Pewaukee, WI (US); William Murray Stoval, III, Draper, UT (US)

(73) Assignee: General Electric Company, Schenectady, NY (US)

( * ) Notice: Subject to any disclaimer, the term of this patent is extended or adjusted under 35 U.S.C. 154(b) by 253 days.

(21) Appl. No.: 11/692,448

(22) Filed: Mar. 28, 2007

(65) Prior Publication Data

US 2008/0243896 A1    Oct. 2, 2008

(51) Int. Cl.
*G06Q 50/00* (2006.01)
*G06F 19/00* (2006.01)

(52) U.S. Cl. ............................................. 705/2; 705/3

(58) Field of Classification Search .................. 705/2–3
See application file for complete search history.

(56) References Cited

U.S. PATENT DOCUMENTS

| | | | |
|---|---|---|---|
| 5,786,816 A * | 7/1998 | Macrae et al. | 715/837 |
| 6,463,346 B1 * | 10/2002 | Flockhart et al. | 700/102 |
| 6,678,703 B2 | 1/2004 | Rothschild et al. | |
| 6,685,642 B1 | 2/2004 | Garg et al. | |
| 6,947,040 B2 | 9/2005 | Tek et al. | |
| 6,988,088 B1 | 1/2006 | Miikkulainen et al. | |
| 7,133,937 B2 | 11/2006 | Leavitt | |
| 7,443,303 B2 * | 10/2008 | Spear et al. | 340/573.1 |
| 2006/0109961 A1 * | 5/2006 | Mahesh et al. | 379/93.25 |
| 2006/0122865 A1 * | 6/2006 | Preiss et al. | 705/2 |
| 2007/0129983 A1 * | 6/2007 | Scherpbier et al. | 705/8 |

FOREIGN PATENT DOCUMENTS

WO    WO2007020601    *    2/2007

OTHER PUBLICATIONS

Dustdar, Mining of ad-hoc business processes with TeamLog, Data & Knowledge Engineering, vol. 55, Issue 2 (Nov. 2005), pp. 129-158, Year of Publication: 2005, ISSN:0169-023X.*
Dazzi, A patient workflow management system built on guidelines, Proc AMIA Annu Fall Symp. 1997: 146-150.*
Son, Improving the performance of time-constrained workflow processing, Journal of Systems and Software, vol. 58, Issue 3, Sep. 15, 2001, pp. 211-219.*
Dazzi, A patient workflow manaclement system built on cluidelines, Proc AMIA Annu Fall Svmp. 1997:146-150.*
Erik Price, et al., U.S. Appl. No. 11/283,417, Pub. Date Jun. 8, 2007.
S. Dustar, et al., "Mining . . . with TeamLog", Technical University of Vienna, Jul. 23, 2004.
Koninklijke Philips Electronics N.V., Pub. # WO/2007/020601, Pub. Date Feb. 22, 2007.
Steven E. Spear et al., U.S. Patent 7,443,303, issued Oct. 28, 2008 (Hill-Rom Inc., assignee).
H.J. Scherbier, U.S. Appl. No. 11/549,253, Pub. Date Jun. 7, 2007, (Siemens, assignee).

* cited by examiner

*Primary Examiner*—Luke Gilligan
*Assistant Examiner*—Tran Nguyen
(74) *Attorney, Agent, or Firm*—McAndrews, Held & Malloy, Ltd.; Michael A. Dellapenna

(57) ABSTRACT

Certain embodiments of the present invention provide a clinical information workflow profiling system including a workflow engine adapted to collect profiling data for a healthcare workflow task and a profiling processor adapted to analyze the profiling data to determine an alternative configuration of the healthcare workflow task.

20 Claims, 2 Drawing Sheets

SYSTEMS AND METHODS FOR PROFILING CLINIC WORKFLOW

BACKGROUND OF THE INVENTION

The present invention generally relates to healthcare workflow. More specifically, the present invention relates to systems and methods for profiling clinic workflow.

Hospitals and other medical facilities, such as, imaging centers and clinics, continually seek to improve or optimize utilization of resources and productivity in their workflows. For example, a clinic may have a workflow for admitting a patient. As another example, a workflow may correspond to a care plan for treating a patient with a particular disease.

Current systems may utilize a workflow engine as a central component of a clinical information system. The workflow engine may be implemented as a standard Business Process Management (BPM) system. Alternatively, various components maybe used in combination to serve a similar purpose.

The purpose of the workflow engine within a complex enterprise system is to manage interactions between people and system components, referred to as actors, performing different roles. In the case of healthcare workflow, the actors operate together to provide healthcare services. These interactions are often complex, and each role may be dependent upon the completion of other tasks or subtasks performed by other actors or occurrences of external events. The workflow engine may be used for both synchronous and asynchronous workflow management. Planning and programming these workflow interactions into the workflow engine is a major task, often taking many months.

In current systems, healthcare practitioner workflow is managed either manually or by static configurations of healthcare information systems. Measuring the actual efficacy of a workflow with current systems is manual, tedious, and ad hoc, and results in poor feedback of improvements into the system.

Thus, a need exists for systems and methods for profiling clinic workflow.

BRIEF SUMMARY OF THE INVENTION

Certain embodiments of the present invention provide a clinical information workflow profiling system including a workflow engine adapted to collect profiling data for a healthcare workflow task and a profiling processor adapted to analyze the profiling data to determine an alternative configuration of the healthcare workflow task.

Certain embodiments of the present invention provide a method for profiling workflow in a healthcare environment including collecting profiling data for a healthcare workflow task, analyzing the profiling data, and determining an alternative configuration of the healthcare workflow task based at least in part on analysis of the profiling data.

Certain embodiments of the present invention provide a computer-readable medium including a set of instructions for execution on a computer, the set of instructions including a collection routine adapted to collect profiling data for a healthcare workflow task, an analysis routine adapted to analyzing the profiling data, and a configuration routine adapted to determine an alternative configuration of the healthcare workflow task based at least in part on analysis of the profiling data.

Figure 1:
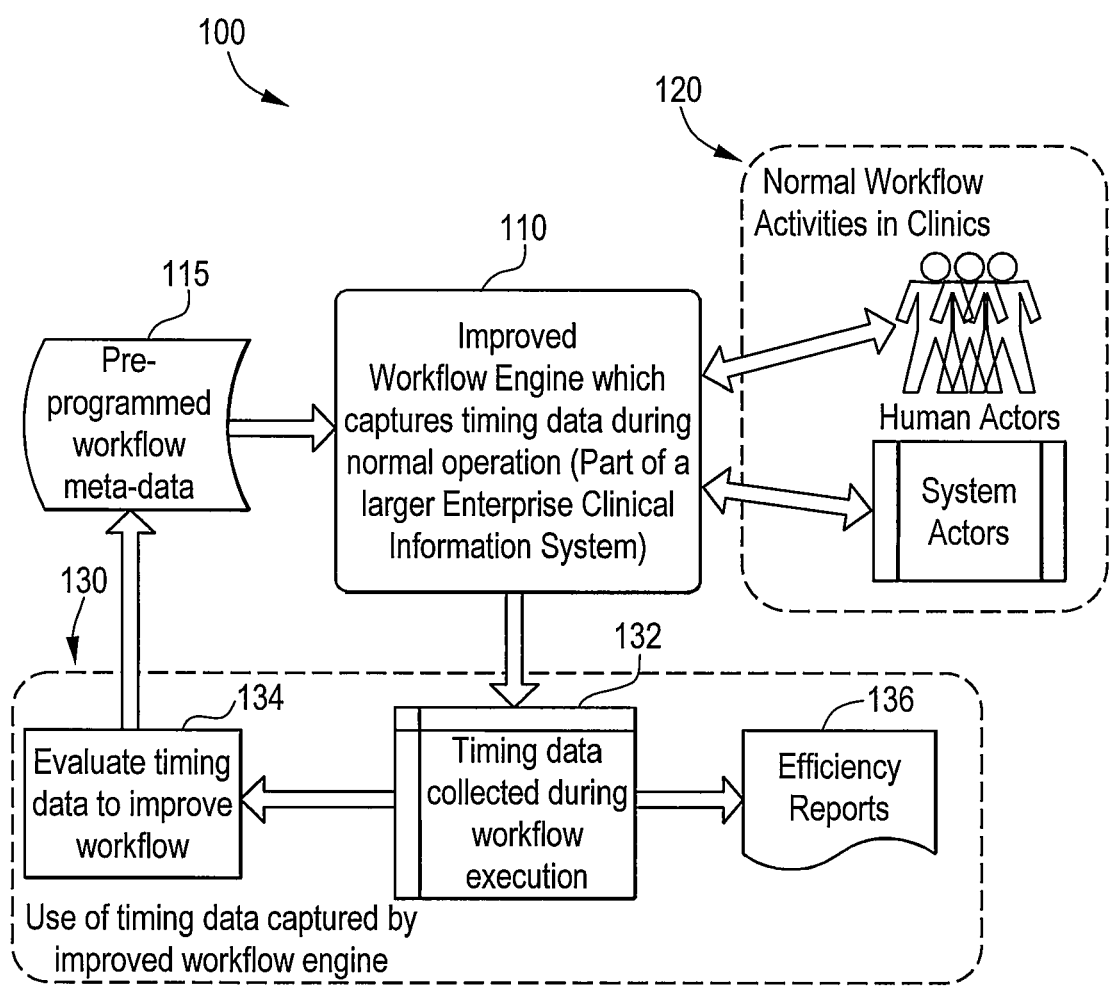
FIG. 1 illustrates a system for profiling clinic workflow according to an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a system 100 for profiling clinic workflow according to an embodiment of the present invention. The system 100 includes a workflow engine 110, workflow actors 120, and a profiling processor 130.

The profiling processor 130 is in communication with the workflow engine 110. The workflow engine 110 is in communication with the workflow actors 120.

In operation, the workflow actors 120 engage in one or more clinic workflow tasks. The workflow actors 120 may include human actors, for example. For example, the human actors may include physicians and nurses. The workflow actors 120 may include system actors. For example, the system actors may include imaging and diagnostic systems. For example, a workflow task may include registering a patient at a clinic. As another example, a care plan to treat a patient with diabetes may be modeled as a workflow task.

The workflow actors 120 may operate together to provide healthcare services through the completion of a workflow task, for example. A workflow may include one or more tasks or subtasks. These tasks or subtasks may be performed by one or more workflow actors 120, each performing a role for a given task or subtask. The workflow actors 120 may interact to complete these tasks. Each role may be dependent upon the completion of other tasks or subtasks performed by other workflow actors 120 or occurrences of external events, for example.

The workflow engine 110 is adapted to collect profiling data for a workflow task. The workflow task may be a healthcare workflow task, for example. The workflow task may include one or more tasks or subtasks, arranged and/or ordered in a configuration. That is, the configuration of a workflow task includes the constituent tasks/subtasks and the ordering, arrangement, relationship, dependencies, and/or interaction of those tasks/subtasks. A workflow task may include several actions, some of which are performed sequentially (synchronous) and some of which are performed in parallel (asynchronous). The workflow task, including each tasks/subtasks, may be performed by one or more workflow actors 120, as discussed above. Information about the workflow task may be represented by workflow metadata 115, for example.

In certain embodiments, the workflow engine 110 may be a modified workflow engine in an existing clinical information system, such as a Business Process Management (BPM)

system. In certain embodiments, the workflow engine 110 may be part of a larger enterprise clinical information system.

The profiling data collected by the workflow engine 110 may include timing data. The timing data may include start and/or end times for one or more events or actions in the workflow task, for example. For example, the timing data may include the time that a subtask in the workflow task was started. As another example, the timing data may include the time that lab results were received. As another example, the timing data may include the time that a test result was sent to a physician's worklist for review. As another example, the timing data may include the elapsed time between a physician's review of a patient's documentation and making test recommendations. The timing data may include time lags, differentials, and/or gaps. For example, the timing data may include the time lag between the completion of one task and the start of a second task in the workflow task. The timing data may include the time between events, the time to achieve a goal, or time wasted between tasks or waiting on unnecessary tasks.

The profiling data collected by the workflow engine 110 may include actor data. The actor data may include which actor, such as a person, department, or group, performed a particular subtask or resulted in a particular event occurring, for example.

The profiling processor 130 is adapted to analyze the profiling data collected by the workflow engine 110. The profiling processor 130 is adapted to determine an alternative configuration for a workflow task.

The profiling processor 130 may determine the alternative configuration in a variety of ways. The profiling processor 130 may analyze the profiling data to determine that two tasks that are currently configured to be performed sequentially may be performed in parallel, for example. For example, the profiling processor 130 may identify that two subtasks have no dependency relationship with each other and that those subtasks are performed by different actors. Thus, the subtasks could be configured to be performed at the same in an alternative configuration of a workflow tasks. As another example, the profiling processor 130 may identify two subtasks being performed by the same actor, and thus must be performed sequentially, that if performed by two different actors, could be performed in parallel.

The profiling processor 130 may analyze the profiling data to determine that two or more sequentially configured tasks in a workflow may be performed in a different sequence to reduce the total time spent performing the workflow task. For example, a workflow task may include two subtasks, the first to collect temperature and blood pressure data for a patient. The second subtask may include having a patient fill out a questionnaire and entering that questionnaire data into a records management system. Both sets of data may be utilized by down-stream tasks in the workflow task. The workflow task may have the collection of the temperature and blood pressure data occur before the patient fills out the questionnaire. However, filling out and processing the questionnaire may take longer than collecting and entering the temperature and blood pressure data. Thus, the profiling processor may determine that these sequential tasks may be performed in a different order so as to reduce the overall time to complete both subtasks. That is, by having the patient fill out the questionnaire and begin the processing before collecting the temperature and blood pressure data, a net savings in time may be achieved.

The profiling processor 130 may analyze the profiling data to determine unnecessary tasks and/or dependencies. For example, a particular subtask may regularly be skipped. The subtask may be determined to be unnecessary if it is skipped some percentage of time above a threshold. For example, if a task is skipped 90% of the time, it may be determined to be unnecessary or optional for the purposes of determining an alternative configuration of the workflow. A dependency may be determined to be unnecessary if a task that is configured to depend on another task is performed at least in part in parallel with the task. This may be determined based on the start and end times of the two tasks. Thus, even though a task is configured in the workflow task to depend on a second task, if those two tasks are actually overlapped in time when performed, the dependency may be determined to be unnecessary.

In certain embodiments, the profiling processor 130 determines permutations and/or combinations for the tasks, subtasks, timing data, and actor data as part of its analysis of the profiling data. By determining the total time for the different permutations and/or combinations, the profiling processor 130 can determine alternative configurations for a workflow task that take less time, and thus may be more efficient.

In certain embodiments, the profiling processor 130 includes a collection component 132. The collection component 132 is adapted to collect profiling data, as discussed above. For example, the collection component 132 may collect timing data. The timing data may be collected during the execution of a workflow task, for example. The timing data may be similar to the timing data, described above, for example.

In certain embodiments, the profiling processor 130 includes an evaluation processor 134. The evaluation processor 134 is adapted to evaluate profiling data. The profiling data may be the timing data collected by the collection component 132, discussed above, for example. The evaluation processor 134 may perform the analysis for the profiling processor 130, for example.

In certain embodiments, the profiling processor 130 includes a report component 136. In certain embodiments, the report component 136 is adapted to provide one or more alternative workflow configurations to a user. The user may be a system administrator, for example. The alternative workflow configurations may be based at least in part on the analysis of the profiling data performed by the profiling processor 130, for example.

In certain embodiments, the report component 136 is adapted to provide statistics for a workflow task. The statistics may be provided to a user, for example. The statistics may be based at least in part on the profiling data, discussed above, for example. For example, statistics may include averages, variations, standard deviations, and estimates for task, subtask, event, and/or action times. For example, statistics may be gathered on the time it takes a particular actor to perform a task. These statistics in turn may be used to identify whether a person may need more training to perform a task faster, for example. As another example, statistics may be used to evaluate whether a particular class of patient takes more time, on average, to complete a workflow task, than another class of patient. In certain embodiments, the statistics may be provided as part of an efficiency report. The efficiency report may cover one or more workflow tasks, for example. The efficiency report may be used by management to identify areas for improvement, including introducing new technologies, automation, staff, or training, for example.

In certain embodiments, the report component 136 provides an estimate of time savings that would result from an alternative configuration of a workflow. A user may utilize the estimate of time savings to decide whether to implement the alternative configuration. The user may implement the alternative configuration in a test mode or a live mode, for example, to increase efficiency.

In certain embodiments, the report component 136 is adapted to provide a recommendation. The recommendation may be provided to a user, for example. The recommendation may be based at least in part on analysis of the profiling data, discussed above, for example. For example, the recommendation may be for a determined alternative configuration for a workflow that is estimated to take less total time than the current workflow.

The components, elements, and/or functionality of system 100 may be implemented alone or in combination in various forms in hardware, firmware, and/or as a set of instructions in software, for example. Certain embodiments may be provided as a set of instructions residing on a computer-readable medium, such as a memory or hard disk, for execution on a general purpose computer or other processing device.

Figure 2:
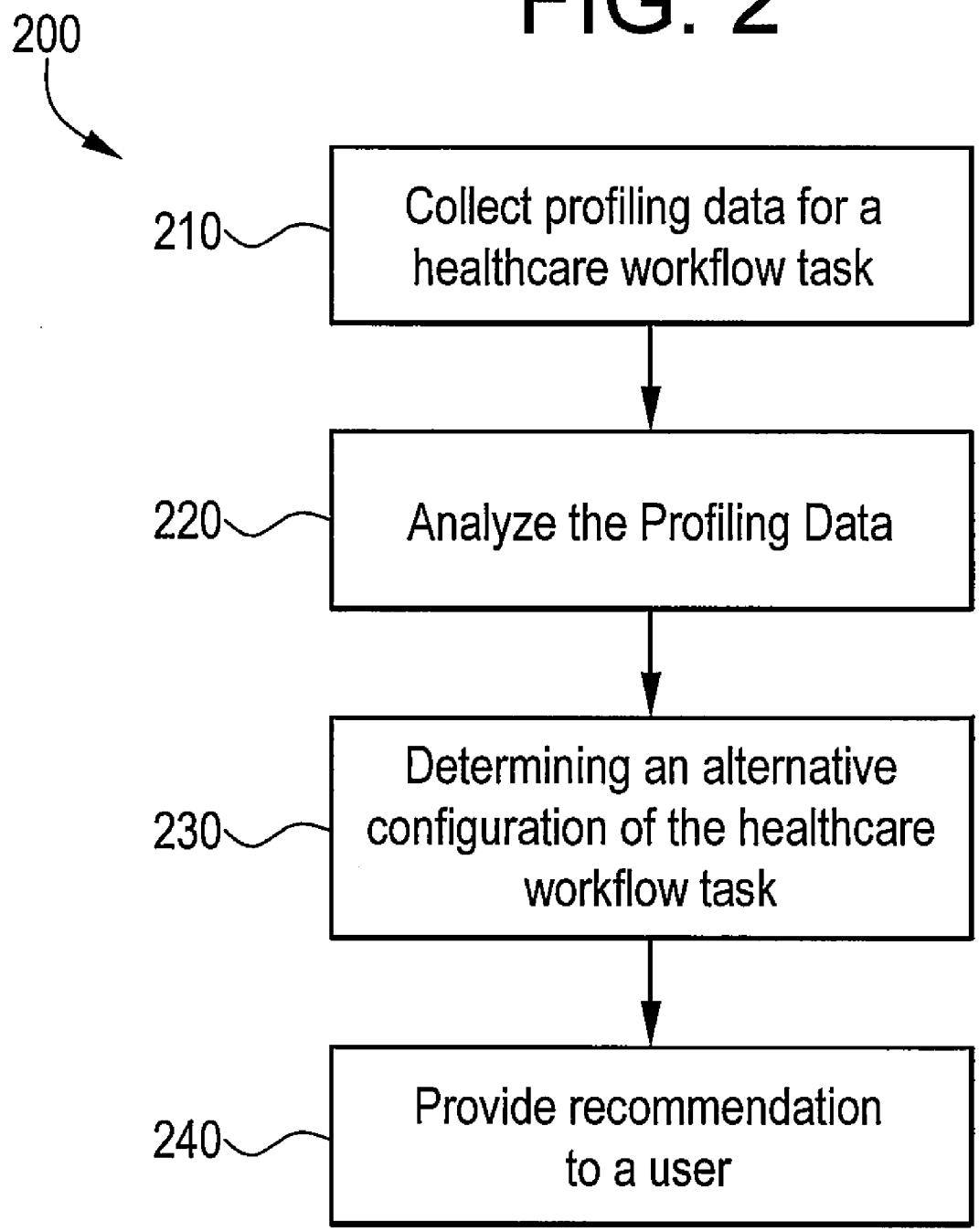
FIG. 2 illustrates a flow diagram for a method for profiling workflow in a healthcare environment according to an embodiment of the present invention.

FIG. 2 illustrates a flow diagram for a method 200 for profiling workflow in a healthcare environment according to an embodiment of the present invention. The method 200 includes the following steps, which will be described below in more detail. At step 210, profiling data for a healthcare workflow task is collected. At step 220, the profiling data is analyzed. At step 230, an alternative configuration of the healthcare workflow task is determined. At step 240, a recommendation is provided to a user. The method 200 is described with reference to elements of systems described above, but it should be understood that other implementations are possible.

At step 210, profiling data for a healthcare workflow task is collected. The profiling data may be collected by a workflow engine similar to the workflow engine 110, described above, for example. The profiling data may be similar to the profiling data, discussed above, for example. The collected profiling data may include timing data. The timing data may include start and/or end times for one or more events or actions in the workflow task, for example. For example, the timing data may include the time that a subtask in the workflow task was started. As another example, the timing data may include the time that lab results were received. As another example, the timing data may include the time that a test result was sent to a physician's worklist for review. As another example, the timing data may include the elapsed time between a physician's review of a patient's documentation and making test recommendations. The timing data may include time lags, differentials, and/or gaps. For example, the timing data may include the time lag between the completion of one task and the start of a second task in the workflow task. The timing data may include the time between events, the time to achieve a goal, or time wasted between tasks or waiting on unnecessary tasks.

The collected profiling data may include actor data. The actor data may include which actor, such as a person, department, or group, performed a particular subtask or resulted in a particular event occurring, for example.

At step 220, the profiling data is analyzed. The profiling data may be analyzed by a profiling processor similar to profiling processor 130, described above, for example. The profiling data may be analyzed by an evaluation processor similar to the evaluation processor 134, described above, for example.

The profiling data may be analyzed to determine that two tasks that are currently configured to be performed sequentially may be performed in parallel, for example. For example, two subtasks that have no dependency relationship with each other and that those subtasks are performed by different actors may be identified. Thus, the subtasks could be configured to be performed at the same in an alternative configuration of a workflow tasks. As another example, two subtasks may be identified that are being performed by the same actor, and thus must be performed sequentially, that if performed by two different actors could be performed in parallel.

The profiling data may be analyzed to determine that two or more sequentially configured tasks in a workflow may be performed in a different sequence to reduce the total time spent performing the workflow task, for example. For example, a workflow task may include two subtasks, the first to collect temperature and blood pressure data for a patient. The second subtask may include having a patient fill out a questionnaire and entering that questionnaire data into a records management system. Both sets of data may be utilized by down-stream tasks in the workflow task. The workflow task may have the collection of the temperature and blood pressure data occur before the patient fills out the questionnaire. However, filling out and processing the questionnaire may take longer than collecting and entering the temperature and blood pressure data. Thus, the profiling processor may determine that these sequential tasks may be performed in a different order so as to reduce the overall time to complete both subtasks. That is, by having the patient fill out the questionnaire and begin the processing before collecting the temperature and blood pressure data, a net savings in time may be achieved.

The profiling data may be analyzed to determine unnecessary tasks and/or dependencies. For example, a particular subtask may regularly be skipped. The subtask may be determined to be unnecessary if it is skipped some percentage of time above a threshold. For example, if a task is skipped 90% of the time, it may be determined to be unnecessary or optional for the purposes of determining an alternative configuration of the workflow. A dependency may be determined to be unnecessary if a task that is configured to depend on another task is performed at least in part in parallel with the task. This may be determined based on the start and end times of the two tasks. Thus, even though a task is configured in the workflow task to depend on a second task, if those two tasks are actually overlapped in time when performed, the dependency may be determined to be unnecessary.

At step 230, an alternative configuration of the healthcare workflow task is determined. The alternative configuration may be determined by a profiling processor similar to the profiling processor 130, described above, for example. The alternative configuration may be determined by an evaluation processor similar to the evaluation processor 134, described above, for example.

The alternative configuration may be determined based at least in part on the profiling data analyzed at step 220, described above, for example. For example, the profiling data may be analyzed by determining permutations and/or combinations for the tasks, subtasks, timing data, and actor data as part of its analysis of the profiling data. By determining the total time for the different permutations and/or combinations, alternative configurations for a workflow task that take less time, and thus may be more efficient, can be determined.

The alternative configuration may be based on performing tasks in parallel or in a different order, for example, as discussed above. The alternative configuration may be based on removing or making optional tasks and/or dependencies identified as being unnecessary or infrequently performed, for example, as discussed above.

At step 240, a recommendation is provided to a user. The recommendation may be provided to the user by a profiling processor similar to profiling processor 130, described above, for example. The recommendation may be provided to the user by a report component similar to the report component 136, described above, for example. The recommendation may be based at least in part on analysis of the profiling data performed at step 220, discussed above, for example. The recommendation may be based at least in part on the alternative configuration determined at step 230, discussed above, for example. For example, the recommendation may be for a determined alternative configuration for a workflow that is estimated to take less total time than the current workflow.

One or more of the steps of the method 200 may be implemented alone or in combination in hardware, firmware, and/or as a set of instructions in software, for example. Certain embodiments may be provided as a set of instructions residing on a computer-readable medium, such as a memory or hard disk, for execution on a computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Thus, certain embodiments of the present invention provide systems and methods for profiling clinic workflow. Certain embodiments provide a technical effect of profiling clinic workflow.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A clinical information workflow profiling system, the system including:
   a workflow engine configured to collect profiling data for a healthcare workflow task comprising a plurality of healthcare workflow actions performed in a first sequence, the profiling data comprising healthcare workflow actor data that includes information about healthcare workflow actors that operate together to complete the healthcare workflow actions in the healthcare workflow task; and
   a profiling processor comprising a computer processor in communication with the workflow engine, the computer processor configured to reorganize the healthcare workflow actions using the healthcare workflow actor data to determine an alternative configuration of the healthcare workflow task that can reduce the total time to perform the healthcare workflow task, the alternative configuration providing a sequence of performing the plurality of healthcare workflow actions that is different than the first sequence, wherein the computer processor is configured to determine whether the healthcare workflow action is skipped at least a threshold percentage of the time that the healthcare workflow task has been previously executed and wherein the computer processor is configured such that, if the healthcare workflow action was skipped at least the threshold percentage of the time that the healthcare workflow task has been previously executed, the alternative configuration for the healthcare workflow task will provide for skipping the healthcare workflow action.

2. The system of claim 1, wherein the computer processor is configured to identify two healthcare workflow actions that are performed in sequence by a single healthcare workflow actor and reorganize the healthcare workflow actions to be performed in parallel by two healthcare workflow actors.

3. The system of claim 1, wherein the profiling data includes a length of time to complete the healthcare work flow actions, and wherein the computer processor is configured to reorganize the healthcare workflow actions such that a healthcare work flow action that takes longer to complete is started before a healthcare work flow action that takes less time to complete.

4. The system of claim 1, wherein the computer processor is configured to identify two healthcare workflow actions that are performed in sequence by different healthcare workflow actors and reorganize the healthcare workflow actions to be performed in parallel.

5. The system of claim 1, further including a report component adapted to provide statistics for the healthcare workflow task, wherein the statistics are based at least in part on the healthcare workflow actor data and a length of time it takes an actor to complete a healthcare workflow action, and wherein the statistics identify a healthcare workflow actor that takes more than an average amount of time to complete a healthcare workflow action.

6. The system of claim 1, further including a report component adapted to provide a recommendation to a user to use the alternative configuration of the healthcare workflow task.

7. The system of claim 1, wherein said profiling processor is configured to use the profiling data to determine an efficiency level of the alternative configuration.

8. A method for profiling workflow in a healthcare environment, the method including:
   collecting profiling data for a healthcare workflow task comprising a plurality of healthcare workflow actions performed in a first sequence, the profiling data comprising healthcare workflow actor data that includes information about healthcare workflow actors that operate together to complete the healthcare workflow actions in the healthcare workflow task; and
   using a processor to reorganize the healthcare workflow actions using the healthcare workflow actor data to determine an alternative configuration of the healthcare workflow task that can reduce the total time to perform the healthcare workflow task, the alternative configuration providing a sequence of performing the plurality of healthcare workflow actions that is different than the first sequence, wherein the processor is configured to determine whether the healthcare workflow action is skipped at least a threshold percentage of the time that the healthcare workflow task has been previously executed, and wherein the profiling processor is configured such that, if the healthcare workflow action was skipped at least the threshold percentage of the time that the healthcare workflow task has been previously executed the alternative configuration for the healthcare workflow task will provide for skipping the healthcare workflow action.

9. The method of claim 8, further comprising using the at least one processor to identify two healthcare workflow actions that are performed in sequence by a single healthcare workflow actor and reorganize the healthcare workflow actions to be performed in parallel by two workflow actors.

10. The method of claim 8, wherein the profiling data includes a length of time to complete the healthcare work flow actions, and wherein the processor is configured to reorganize the healthcare workflow actions such that a healthcare work flow action that takes longer to complete is started before a healthcare work flow action that takes less time to complete.

11. The method of claim 8, wherein the processor is configured to identify two healthcare workflow actions that are performed in sequence by different healthcare workflow actors and reorganize the healthcare workflow actions to be performed in parallel.

12. The method of claim 8, further including providing statistics for the healthcare workflow task, wherein the statistics are based at least in part on the healthcare workflow actor data and a length of time it takes an actor to complete a healthcare workflow action, and wherein the statistics identify a healthcare workflow actor that takes more than an average amount of time to complete a healthcare workflow action.

13. The method of claim 8, further including a providing a recommendation to a user to use the alternative configuration of the healthcare workflow task.

14. A non-transitory computer-readable medium including a set of instructions for execution on a computer, the set of instructions including:
   a collection routine adapted to collect profiling data for a healthcare workflow task comprising a plurality of healthcare workflow actions performed in a first sequence, the profiling data comprising healthcare workflow actor data that includes information about healthcare workflow actors that operate together to complete the healthcare workflow actions in the healthcare workflow task; and
   a configuration routine adapted to reorganize the healthcare workflow actions using the healthcare workflow actor data to determine an alternative configuration of the healthcare workflow task that can reduce the total time to perform the healthcare workflow task, the alternative configuration providing a sequence of performing the plurality of healthcare workflow actions that is different than the first sequence, wherein the configuration routine is adapted to determine whether the healthcare workflow action is skipped at least a threshold percentage of the time that the healthcare workflow task has been previously executed, and wherein the profiling processor is configured such that, if the healthcare workflow action was skipped at least the threshold percentage of the time that the healthcare workflow task has been previously executed, the alternative configuration for the healthcare workflow task will provide for skipping the healthcare workflow action.

15. The medium and instructions of claim 14, wherein the configuration routine is adapted to identify two healthcare workflow actions that are performed in sequence by a single healthcare workflow actor and reorganize the healthcare workflow actions to be performed in parallel by two healthcare workflow actors.

16. The medium and instructions of claim 14, wherein the profiling data includes a length of time to complete the healthcare work flow actions, and wherein the configuration routine is adapted to reorganize the healthcare workflow actions such that a healthcare work flow action that takes longer to complete is started before a healthcare work flow action that takes less time to complete.

17. The medium and instructions of claim 14, wherein the configuration routine is configured to identify two healthcare workflow actions that are performed in sequence by different healthcare workflow actors and reorganize the healthcare workflow actions to be performed in parallel.

18. The medium and instructions of claim 14, further including a report routine adapted to provide statistics for the healthcare workflow task, wherein the statistics are based at least in part on the healthcare workflow actor data and a length of time it takes an actor to complete a healthcare workflow action, and wherein the statistics identify a healthcare workflow actor that takes more than an average amount of time to complete a healthcare workflow action.

19. The medium and instructions of claim 14, further including a report routine adapted to provide a recommendation to a user to use the alternative configuration of the healthcare workflow task.

20. The medium and instructions of claim 14, wherein the configuration routine is adapted to use the profiling data to determine an efficiency level of the alternative configuration.

* * * * *